US012226472B2

(12) United States Patent
Tian et al.

(10) Patent No.: US 12,226,472 B2
(45) Date of Patent: Feb. 18, 2025

(54) FOOT-AND-MOUTH DISEASE VIRUS-LIKE PARTICLE ANTIGEN, AND VACCINE COMPOSITION, PREPARATION METHOD, AND APPLICATION THEREOF

(71) Applicant: PULIKE BIOLOGICAL ENGINEERING, INC., Henan (CN)

(72) Inventors: Kegong Tian, Henan (CN); Yan Xiao, Henan (CN); Wenqiang Pang, Henan (CN); Jinzhong Sun, Henan (CN); Xuke Zhang, Henan (CN)

(73) Assignee: PULIKE BIOLOGICAL ENGINEERING, INC., Henan (CN)

( * ) Notice: Subject to any disclaimer, the term of this patent is extended or adjusted under 35 U.S.C. 154(b) by 810 days.

(21) Appl. No.: 17/421,541

(22) PCT Filed: Jan. 15, 2019

(86) PCT No.: PCT/CN2019/071813
§ 371 (c)(1),
(2) Date: Jul. 8, 2021

(87) PCT Pub. No.: WO2020/147015
PCT Pub. Date: Jul. 23, 2020

(65) Prior Publication Data

US 2022/0096620 A1 Mar. 31, 2022

(51) Int. Cl.

*A61K 39/135* (2006.01)
*A61K 39/00* (2006.01)
*A61P 31/14* (2006.01)
*C07K 14/005* (2006.01)

(52) U.S. Cl.

CPC ............ *A61K 39/135* (2013.01); *A61P 31/14* (2018.01); *C07K 14/005* (2013.01); *A61K 2039/5258* (2013.01); *A61K 2039/55577* (2013.01)

(58) Field of Classification Search

CPC .......... A61K 39/135; A61K 2039/5258; A61K 2039/55577; A61P 31/14; C07K 14/005
See application file for complete search history.

(56) References Cited

U.S. PATENT DOCUMENTS

| | | | | |
|---|---|---|---|---|
| 2,909,462 | A | 10/1959 | Warfield et al. | |
| 10,010,605 | B2 * | 7/2018 | Audonnet | A61K 39/135 |
| 10,894,081 | B2 * | 1/2021 | Zheng | C12N 7/00 |

FOREIGN PATENT DOCUMENTS

| | | | | | |
|---|---|---|---|---|---|
| CN | 105624124 | A | * | 6/2016 | |
| CN | 106148290 | A | | 11/2016 | |
| CN | 106479986 | A | | 3/2017 | |
| CN | 106540248 | A | | 3/2017 | |
| CN | 107029226 | A | | 8/2017 | |
| CN | 107236747 | A | | 10/2017 | |
| CN | 110777160 | A | * | 2/2020 | A61K 39/12 |
| CN | 111233984 | A | * | 6/2020 | A61K 39/12 |
| WO | 2020147015 | A1 | | 7/2020 | |

OTHER PUBLICATIONS

Zhang et al. CN 105624124 A. Machine Translation. (Year: 2016).*
Tian et al. CN 110777160 A. Machine Translation. (Year: 2020).*
Tian et al. CN 111233984 A. Machine Translation. (Year: 2020).*
Rweyemamu, M. M., Terry, G., & Pay, T. W. (1979). Stability and immunogenicity of empty particles of foot-and-mouth disease virus. Archives of virology, 59(1-2), 69-79. (Year: 1979).*
Goodwin, S. et al. (2009). Foot-and-mouth disease virus assembly: processing of recombinant capsid precursor by exogenous protease induces self-assembly of pentamers in vitro in a myristoylation-dependent manner. Journal of virology, 83(21), 11275-11282. (Year: 2009).*
Written Opinion of the International Searching Authority. PCT/CN2019/071813. Jun. 4, 2019. English Translation. (Year: 2019).*
Heise, M., et al. (2023). Adjuvant-dependent effects on the safety and efficacy of inactivated SARS-CoV-2 vaccines during heterologous infection by a SARS-related coronavirus. Research square, rs.3.rs-3401539. (Year: 2023).*
Lidgate, D.M. (2000). Preparation of the Syntex Adjuvant Formulation (SAF, SAF-m, and SAF-1). In: O'Hagan, D.T. (eds) Vaccine Adjuvants. Methods in Molecular Medicine™, vol. 42, pp. 229-237. Springer, Totowa, NJ. (Year: 2000).*
D2—Di Nardo, Antonello et al., Phylodynamic reconstruction of O CATHAY topotype foot-and-mouth disease virus epidemics in the Philippines, Veterinary Research 2014, vol. 45, article No. 90.

(Continued)

*Primary Examiner* — Rachel B Gill
*Assistant Examiner* — Carey Alexander Stuart
(74) *Attorney, Agent, or Firm* — John A. Miller; Shumaker, Loop & Kendrick, LLP

(57) ABSTRACT

A type O foot-and-mouth disease virus-like particle antigen is provided, wherein the type O foot-and-mouth disease virus-like particle antigen is type O CATHAY topotype foot-and-mouth disease virus-like particle antigen, and the type O CATHAY topotype foot-and-mouth disease virus-like particle antigen is assembled by VP0, VP3 and VP1 antigen proteins of type O CATHAY topotype foot-and-mouth disease virus. The type O foot-and-mouth disease virus-like particle antigen has good immunogenicity. The prepared vaccine can produce complete protection against the O-type foot-and-mouth disease virus on the 14th day after immunization. The antibody titer produced is higher than that of the commercial inactivated vaccine, and the duration of immune protection can be maintained for at least 133 days. The prepared vaccine composition, preparation method and use thereof are also provided.

11 Claims, No Drawings

Specification includes a Sequence Listing.

(56) References Cited

OTHER PUBLICATIONS

D5—Zheng, Haixue et al. Genetic characterization of a new pandemic Southeast Asia topotype strain of serotype O foot-and-mouth disease virus isolated in China during 2010, Virus Genes (2012) vol. 44, issue 1, p. 80-88.
Japan Office Action and machine translation.

* cited by examiner

SEQUENCE LISTING

```
<160> NUMBER OF SEQ ID NOS: 7

<210> SEQ ID NO 1
<211> LENGTH: 909
<212> TYPE: DNA
<213> ORGANISM: Artificial sequence
<220> FEATURE:
<223> OTHER INFORMATION: Synthetic sequence

<400> SEQUENCE: 1

ggtgctggtc agtcttctcc gaccaccggt tctcagaacc agtctggtaa caccggttct      60

atcatcaaca actactacat gcagcagtac cagaactcta tggacaccca gctgggtgac     120

aacgctatct ctggtggttc taacgaaggt tctaccgaca ccacctctac ccacaccaac     180

aacacccaga acaacgactg gttctctaaa ctggctaaca ccgctttctc tggtctgttc     240

ggtgctctgc tggctgacaa aaaaaccgaa gaaaccaccc tgctggaaga ccgtatcctg     300

accacccgta acggtcacac cacctctacc acccagtctt ctgttggtgt tacctacggt     360

tacgctaccg ctgaagactt cgtttctggt ccgaacacct ctggtctgga aacccgtgtt     420

gttcaggctg aacgtttctt caaaacccac ctgttcgact ggggtaccaa cgactctttc     480

ggtcgttgcc acctgctgga actgccgacc gaccacaaag gtgtttacgg ttctctgacc     540

gactcttacg cttacatgcg taacggttgg gacgttgaag ttaccgctgt tggtaaccag     600

ttcaacggtg gttgcctgct ggttgctatg gttccggaac tgcgttctat caccaaacgt     660

gaactgtacc agctgaccct gttcccgcac cagttcatca acccgcgtac caacatgacc     720

gctcacatca ccgttccgta cctgggtgtt aaccgttacg accagtacaa agttcacaaa     780

ccgtggaccc tggttgttat ggttgttgct ccgctgaccg ttaacaacga aggtgctccg     840

cagatcaaag tttacgctaa catcgctccg accaacgttc acgttgctgg tgaactgccg     900

tctaaagaa                                                             909

<210> SEQ ID NO 2
<211> LENGTH: 660
<212> TYPE: DNA
<213> ORGANISM: Artificial sequence
<220> FEATURE:
<223> OTHER INFORMATION: Synthetic sequence

<400> SEQUENCE: 2

ggtatcttcc cggttgcttg ctctgacggt tacggtggtc tggttaccac cgacccgaaa      60

accgctgacc cggtttacgg taaagttttc aacccgccgc gtaacctgct gccgggtcgt     120

ttcaccaacc tgctggacgt tgctgaagct tgcccgacct tcctgcactt cgacggtgac     180

gttccgtacg ttgttaccaa aaccgactct gaccgtgttc tggctcagtt cgacctgtct     240
```

-continued

```
ctggctgcta aacacatgtc taacaccttc ctggctggtc tggctcagta ctacgctcag    300

tactctggta ccatcaacct gcacttcatg ttcaccggtc cgaccgacgc taaagctcgt    360

tacatggttg cttacgctcc gccgggtatg gaaccgccga aaaccccgga agctgctgct    420

cactgcatcc acgctgaatg ggacaccggt ctgaactcta aattcacctt ctctatcccg    480

tacctgtctg ctgctgacta cgcttacacc gcttctgacg ttgctgaaac caccaacgtt    540

cagggttggg tttgcctgtt ccagatcacc cacggtaaag ctgacggtga cgctctggtt    600

gttctggctt ctgctggtaa agacttcgac ctgcgtctgc cggttgacgc tcgtacccag    660


<210> SEQ ID NO 3
<211> LENGTH: 633
<212> TYPE: DNA
<213> ORGANISM: Artificial sequence
<220> FEATURE:
<223> OTHER INFORMATION: Synthetic sequence

<400> SEQUENCE: 3

accacctctg ctggtgaatc tgctgacccg gttaccacca ccgttgaaaa ctacggtggt     60

gaaacccagg ttcagcgtcg tcagcacacc gacgttgctt tcatcctgga ccgtttcgtt    120

aaagttaaac cgcaggaaca ggttaacgtt ctggacctga tgcagatccc ggctcacacc    180

ctggttggtg ctctgctgcg taccgctacc tactacttct ctgacctgga actggctgtt    240

aaacacgaag gtgacctgac ctgggttccg aacggtgctc cggaaaccgc tctggacaac    300

accaccaacc cgaccgctta ccacaaagaa ccgctgaccc gtctggctct gccgtacacc    360

gctccgcacc gtgttctggc taccgtttac aacggttctt ctaaatacgg tgacgcttct    420

accaacaacg ttcgtggtga cctgcaggtt ctggttaaaa aagctgaacg tgctctgccg    480

acctctttca actacggtgc tatcaaagct gctcgtgtta ccgaactgct gtaccgtatg    540

aaacgtgctg aaacctactg cccgcgtccg ctgctggcta tccagccgtc taccgctcgt    600

cacaaacaga aaatcgttgc tccggctaaa cag                                 633


<210> SEQ ID NO 4
<211> LENGTH: 255
<212> TYPE: DNA
<213> ORGANISM: Artificial sequence
<220> FEATURE:
<223> OTHER INFORMATION: Synthetic sequence

<400> SEQUENCE: 4

ggtgctggtc agtcttctcc ggctaccggt tctcagaacc agtctggtaa caccggttct     60

atcatcaaca actactacat gcagcagtac cagaactcta tggacaccca gctgggtgac    120

aacgctatct ctggtggttc taacgaaggt tctaccgaca ccacctctac ccacaccacc    180

aacacccaga acaacgactg gttctctaaa ctggcttctt ctgctttctc tggtctgttc    240

ggtgctctgc tggct                                                     255


<210> SEQ ID NO 5
<211> LENGTH: 654
<212> TYPE: DNA
<213> ORGANISM: Artificial sequence
<220> FEATURE:
<223> OTHER INFORMATION: Synthetic sequence

<400> SEQUENCE: 5

gacaaaaaaa ccgaagaaac caccctgctg gaagaccgta tcctgaccac ccgtaacggt     60
```

-continued

```
cacaccacct ctaccaccca gtcttctgtt ggtatcaccc acggttacgc taccgctgaa    120

gacttcgttt ctggtccgaa cacctctggt ctggaaaccc gtgttatcca ggctgaacgt    180

ttcttcaaaa cccacctgtt cgactgggtt acctctgacc cgttcggtcg ttaccacctg    240

ctggaactgc cgaccgacca caaaggtgtt tacggttctc tgaccgactc ttacgcttac    300

atgcgtaacg gttgggacgt tgaagttacc gctgttggta accagttcaa cggtggttgc    360

ctgctggttg ctatggttcc ggaactgtgc tctatcgaac gtcgtgaact gttccagctg    420

accctgttcc cgcaccagtt catcaacccg cgtaccaaca tgaccgctca catcaaagtt    480

ccgttcgttg gtgttaaccg ttacgaccag tacaaagttc acaaaccgtg gaccctggtt    540

gttatggttg ttgctccgct gaccgttaac accgaaggtg ctccgcagat caaagtttac    600

gctaacatcg ctccgaccaa cgttcacgtt gctggtgaat tcccgtctaa agaa          654


<210> SEQ ID NO 6
<211> LENGTH: 660
<212> TYPE: DNA
<213> ORGANISM: Artificial sequence
<220> FEATURE:
<223> OTHER INFORMATION: Synthetic sequence

<400> SEQUENCE: 6

ggtatcttcc cggttgcttg ctctgacggt tacggtggtc tggttaccac cgacccgaaa     60

accgctgacc cggtttacgg taaagttttc aacccgccgc gtaacatgct gccgggtcgt    120

ttcaccaacc tgctggacgt tgctgaagct tgcccgacct tcctgcactt cgacggtgac    180

gttccgtacg ttaccaccaa aaccgactct gaccgtgttc tggctcagtt cgacctgtct    240

ctggctgcta aacacatgtc taacaccttc ctggctggtc tggctcagta ctacacccag    300

tactctggta ccatcaacct gcacttcatg ttcaccggtc cgaccgacgc taaagctcgt    360

tacatgatcg cttacgctcc gccgggtatg gaaccgccga aaaccccgga agctgctgct    420

cactgcatcc acgctgaatg ggacaccggt ctgaactcta aattcacctt ctctatcccg    480

tacctgtctg ctgctgacta cgcttacacc gcttctggtg ctgctgaaac caccaacgtt    540

cagggttggg tttgcctgtt ccagatcacc cacggtaaag ctgaaggtga cgctctggtt    600

gttctggctt ctgctggtaa agacttcgaa ctgcgtctgc cggttgacgc tcgtcagcag    660


<210> SEQ ID NO 7
<211> LENGTH: 639
<212> TYPE: DNA
<213> ORGANISM: Artificial sequence
<220> FEATURE:
<223> OTHER INFORMATION: Synthetic sequence

<400> SEQUENCE: 7

accacctcta ccggtgaatc tgctgacccg gttaccgcta ccgttgaaaa ctacggtggt     60

gaaacccagg ttcagcgtcg tcaccacacc gacgtttctt tcatcctgga ccgtttcgtt    120

aaagttaccc cgaaagactc tatcaacgtt ctggacctga tgcagacccc gccgcacacc    180

ctggttggtg ctctgctgcg taccgctacc tactacttcg ctgacctgga agttgctgtt    240

aaacacaaag gtgacctgac ctgggttccg aacggtgctc cggaagctgc tctggacaac    300

accaccaacc cgaccgctta ccacaaagct ccgctgaccc gtctggctct gccgtacacc    360

gctccgcacc gtgttctggc taccgtttac aacggtaact gcaaatacgc tggtggttct    420

ctgccgaacg ttcgtggtga cctgcaggtt ctggctcaga aagctgcttg gccgctgccg    480

acctctttca actacggtgc tatcaaagct acccgtgtta ccgaactgct gtaccgtatg    540
```

-continued

```
aaacgtgctg aaacctactg cccgcgtccg ctgctggctg ttcacccgtc tgctgctcgt    600

cacaaacaga aaatcgttgc tccggttaaa cagtctctg                           639
```

FOOT-AND-MOUTH DISEASE VIRUS-LIKE PARTICLE ANTIGEN, AND VACCINE COMPOSITION, PREPARATION METHOD, AND APPLICATION THEREOF

CROSS-REFERENCE TO RELATED APPLICATIONS

This application is a National Stage application of International Application No. PCT/CN2019/071813 filed on Jan. 15, 2019.

SEQUENCE LISTING

This application includes a Sequence Listing that has been provided as an ASCII plain text file and was created on Jul. 8, 2021, has the file name 254860_Sequ (15997890.1) and a file size of 7 KB. This Sequence Listing is hereby incorporated by reference.

BACKGROUND

Field

The present disclosure belongs to a viral antigen and a pharmaceutical preparation of the antigen. Specifically, the present disclosure relates to a foot-and-mouth disease virus-like particle antigen, a vaccine composition prepared therefrom, and a preparation method and application thereof.

Discussion of the Related Art

Foot-and-mouth disease (FMD) is an acute, highly contagious animal disease that can quickly spread over long distances and is the most infectious disease for mammals, among which infection in cloven-hoofed animals will cause significant economic losses globally. Animals suffering from foot-and-mouth disease include cattle, sheep and swine. A pathogenic factor is Foot-and-Mouth Disease Virus (FMDV), which is an aphthovirus belonging to the picornavirus family. The virus has 7 serotypes (types A, O, C, Asia 1, SAT1, SAT2 and SAT3), among which type O foot-and-mouth disease virus is the most widespread. According to genetic classification, there are currently three major genetic topotypes of type-O foot-and-mouth disease viruses in China, i.e. CATHAY topotype (Chinese type), ME-SA topotype (Middle East-South Asia type) and SEA topotype (Southeast Asian type). Vaccination is an effective measure to control this disease and protect livestock from harm.

However, inactivated type O foot-and-mouth disease virus antigen is weakly antigenic, and the existing inactivated type O foot-and-mouth disease virus vaccine often requires two times of immunization to provide protection. Virus-like particles (VLPs) are particles similar to viruses, that can self assemble into virus shell structures when expressed in vitro and/or in vivo, and are pseudoviruses that have similar shell structures of viruses but do not have the ability to replicate. VLPs vaccine can effectively stimulate the body to produce anti-infection and anti-tumor immunity. A vaccine based on virus-like particles is an ideal form of vaccine. However, there is no report on practical application of type O foot-and-mouth disease virus-like particle vaccine.

In addition, there are great variations in antigens of the CATHAY topotype variants that are popular in China, and the existing vaccines have significantly reduced protection against the CATHAY topotype variants. In addition, their immunogenicity is weak and cannot induce sufficient immunity in animals. Therefore, it is an urgent task to screen out ideal strain sequences to prepare virus-like particles which also meets the needs of the country to effectively prevent and control major animal diseases and ensure healthy and sustainable development of animal husbandry.

SUMMARY

In order to solve the deficiency of weak immunogenicity of the inactivated type O foot-and-mouth disease virus vaccine in the prior art, the present disclosure provides a type O foot-and-mouth disease virus-like particle antigen, wherein the type O foot-and-mouth disease virus-like particle antigen is type O CATHAY topotype foot-and-mouth disease virus-like particle antigen, and the type O CATHAY topotype foot-and-mouth disease virus-like particle antigen is assembled by VP0, VP3 and VP1 antigen proteins of type O CATHAY topotype foot-and-mouth disease virus.

The foot-and-mouth disease virus-like particle antigen has good immunogenicity, and a single-shot vaccine can provide complete protection against foot-and-mouth disease virus. The foot-and-mouth disease virus-like particle antigen has good stability. After being placed at 4° C. for 3 months, it can be observed through the electron microscope after negative staining with phosphotungstic acid that the virus-like particles are still plump without aggregation.

As an embodiment of the present disclosure, in the type O foot-and-mouth disease virus-like particle antigen of the present disclosure, the VP0 antigen protein of type O CATHAY topotype foot-and-mouth disease virus is encoded by SEQ ID No: 1 or a degenerate sequence thereof; the VP3 antigen protein of type O CATHAY topotype foot-and-mouth disease virus is encoded by SEQ ID No: 2 or a degenerate sequence thereof; and the VP1 antigen protein of type O CATHAY topotype foot-and-mouth disease virus is encoded by SEQ ID No: 3 or a degenerate sequence thereof.

The type O CATHAY topotype foot-and-mouth disease virus-like particle antigen is derived from a current epidemic strain and can produce complete protection against the current epidemic wild strain.

The present disclosure also provides a type O foot-and-mouth disease virus-like particle vaccine, wherein the type O foot-and-mouth disease virus-like particle vaccine comprises the type O CATHAY topotype foot-and-mouth disease virus-like particle antigen and a pharmaceutically acceptable carrier.

The type O—foot-and-mouth disease virus-like particle vaccine of the present disclosure can reach an antibody titer of more than 1:128 on the $14^{th}$ day after immunization, and can provide the long-term maintenance of high antibody titers, which can produce protection for the entire fattening period.

As an embodiment of the present disclosure, in the type O foot-and-mouth disease virus-like particle vaccine of the present disclosure, content of the type O CATHAY topotype foot-and-mouth disease virus-like particle antigen is 160-240 μg/ml.

The content of the type O CATHAY topotype foot-and-mouth disease virus-like particle antigen can be selected from 160 μg/ml, 170 μg/ml, 180 μg/ml, 190 μg/ml, 200 μg/ml, 210 μg/ml, 220 μg/ml, 230 μg/ml, and 240 μg/ml.

Even when the content of the type O CATHAY topotype foot-and-mouth disease virus-like particle antigen is only 160 μg/ml, an antibody titer of above 1:128 can be reached on the $14^{th}$ day after immunization, and long-term high antibody titers can be maintained.

As a preferred embodiment of the present disclosure, in the type O foot-and-mouth disease virus-like particle vaccine of the present disclosure, the content of the type O CATHAY topotype foot-and-mouth disease virus-like particle antigen is 200 μg/ml.

As an embodiment of the present disclosure, in the type O foot-and-mouth disease virus-like particle vaccine of the present disclosure, the pharmaceutically acceptable carrier comprises an adjuvant which comprises one or more of (1) white oil, alhydrogel adjuvant, saponins, Avridine, DDA; (2) water-in-oil emulsion, oil-in-water emulsion, water-in-oil-in-water emulsion; or (3) polymers of acrylic or methacrylic acid, copolymers of maleic anhydride and alkenyl derivative; and the RIBI adjuvant system, Block co-polymer, SAF-M, monophosphoryl lipid A, Avridine lipid-amine adjuvant, heat-labile enterotoxin from *E. coli*, cholera toxin, IMS 1314, muramyl dipeptide, Montanide ISA 206, and Gel adjuvant; preferably, the saponin is Quil A, QS-21 or GPI-0100.

The content of the adjuvant is 5%-60% V/V, preferably 30%-60% V/V, more preferably 50% V/V.

As an embodiment of the present disclosure, the pharmaceutically acceptable carrier includes drugs, immunostimulants, antioxidants, surfactants, colorants, volatile oils, buffers, dispersants, propellants and preservatives; the immunostimulants include α-interferon, β-interferon, γ-interferon, granulocyte-macrophage colony stimulating factor (GM-CSF), macrophage colony stimulating factor (M-CSF) and interleukin 2 (IL2).

To prepare such a composition, methods known in the art can be used.

As an embodiment of the present disclosure, in the O-type foot-and-mouth disease virus-like particle vaccine of the present disclosure, the type O foot-and-mouth disease virus-like particle vaccine further comprises an immunogenic amount of type O SEA topotype foot-and-mouth disease virus-like particle antigen.

The vaccine of the present disclosure is added with type O SEA topotype foot-and-mouth disease virus-like particle antigen, which can produce immune protection against type O CATHAY topotype foot-and-mouth disease and type O SEA topotype foot-and-mouth disease.

As a preferred embodiment of the present disclosure, in the type O foot-and-mouth disease virus-like particle vaccine of the present disclosure, the type O SEA topotype foot-and-mouth disease virus-like particle antigen is assembled by VP4, VP2, VP3 and VP1 antigen proteins of type O SEA topotype foot-and-mouth disease virus.

The type O SEA topotype foot-and-mouth disease virus-like particle antigen has good immunogenicity, and an antibody titer of above 1:128 can be reached on the 14th day after immunization. The type O SEA topotype foot-and-mouth disease virus-like particle antigen has good stability. After being placed at 4° C. for 3 months, it can be observed through the electron microscope after negative staining with phosphotungstic acid that the virus-like particles are still plump without aggregation.

As an embodiment of the present disclosure, in the type O foot-and-mouth disease virus-like particle vaccine of the present disclosure, the VP4 antigen protein of the type O SEA topotype foot-and-mouth disease virus is encoded by SEQ ID No: 4 or a degenerate sequence thereof; the VP2 antigen protein of the type O SEA topotype foot-and-mouth disease virus is encoded by SEQ ID No: 5 or a degenerate sequence thereof; the VP3 antigen protein of the type O SEA topotype foot-and-mouth disease virus is encoded by SEQ ID No: 6 or a degenerate sequence thereof; and the VP1 antigen protein of the type O SEA topotype foot-and-mouth disease virus is encoded by SEQ ID No: 7 or a degenerate sequence thereof.

As an embodiment of the present disclosure, in the type O foot-and-mouth disease virus-like particle vaccine of the present disclosure, content of the type O SEA topotype foot-and-mouth disease virus-like particle antigen is 160-240 μg/ml.

The content of the type O SEA topotype foot-and-mouth disease virus-like particle antigen can be selected from 160 μg/ml, 170 μg/ml, 180 μg/ml, 190 μg/ml, 200 μg/ml, 210 μg/ml, 220 μg/ml, 230 μg/ml and 240 μg/ml.

As a preferred embodiment of the present disclosure, in the type O foot-and-mouth disease virus-like particle vaccine of the present disclosure, the content of the type O SEA topotype foot-and-mouth disease virus-like particle antigen is 200 μg/ml.

The present disclosure also relates to a method for preparing the type O foot-and-mouth disease virus-like particle vaccine, wherein the method comprises:

Step (1) amplifying and cloning genes of VP0, VP3, VP1 antigen proteins of the type O CATHAY topotype foot-and-mouth disease virus into a common tandem expression vector to obtain a recombinant expression vector containing the genes of VP0, VP3, VP1 antigen proteins of the type O CATHAY topotype foot-and-mouth disease virus;

Step (2) transforming or transducing a host cell with the recombinant expression vector containing the genes of VP0, VP3, VP1 antigen proteins of the type O CATHAY topotype foot-and-mouth disease virus obtained in the step (1) to obtain a recombinant containing the recombinant expression vector;

Step (3) culturing the recombinant obtained in the step (2), expressing VP0, VP3, VP1 antigen proteins of the type O CATHAY topotype foot-and-mouth disease virus in tandem which then self-assemble to form the type O CATHAY topotype foot-and-mouth disease virus-like particle antigen; and Step (4) purifying the type O CATHAY topotype foot-and-mouth disease virus-like particle antigen obtained in the step (3) and adding an adjuvant to obtain the type O foot-and-mouth disease virus-like particle vaccine.

The present disclosure can obtain stable self-assembled virus-like particles by expressing the VP0, VP3, and VP1 antigen proteins of type O CATHAY topotype foot-and-mouth disease virus, and their immune effect can provide complete protection to the swine. In the present disclosure, the VP0, VP3, and VP1 antigen proteins of type O CATHAY topotype foot-and-mouth disease virus are expressed in tandem and then self-assemble to form the type O CATHAY topotype foot-and-mouth disease virus-like particle antigen, which facilitates subsequent purification and separation of antigens.

As an embodiment of the present disclosure, in the method of the present disclosure, the VP0 antigen protein of type O CATHAY topotype foot-and-mouth disease virus is encoded by SEQ ID No: 1 or a degenerate sequence thereof; the VP3 antigen protein of type O CATHAY topotype foot-and-mouth disease virus is encoded by SEQ ID No: 2 or a degenerate sequence thereof; and the VP1 antigen protein of type O CATHAY topotype foot-and-mouth disease virus is encoded by SEQ ID No: 3 or a degenerate sequence thereof; the host cell in the step (2) is *E. coli*; the VP0, VP3, VP1 antigen proteins of the type O CATHAY topotype foot-and-mouth disease virus expressed in the step (3) are intracellular soluble proteins.

The present disclosure uses *E. coli* expression system to produce foot-and-mouth disease virus-like particles, which has the advantages such as high yield, low production cost, good immunogenicity, and no bio-safety risks etc. The virus-like particle vaccine composition prepared in the present disclosure can provide protective activity against type O foot-and-mouth disease, and compared with the existing commercialized inactivated whole virus vaccines, it not only produces antibodies quickly, and produces high levels of antibodies, but also significantly increase duration of immunity and maintain immune protection for a longer time.

The present disclosure also relates to use of the type O foot-and-mouth disease virus-like particle vaccine in preparation of a medicament for preventing and/or treating type O foot-and-mouth disease.

The subject of administration of the medicament for preventing and/or treating foot-and-mouth disease virus infection of the present disclosure includes swine.

DETAILED DESCRIPTION OF THE EMBODIMENTS

Hereinafter, embodiments of the present disclosure will be described.

"Foot-and-mouth disease virus" belongs to Aphthovirus genus of the Picornaviridae family. The virus is classified into seven serotypes, O, A, C, SAT1, SAT2, SAT3 (that is, Southern African Territories 1, 2, 3) and Asia 1, between each of which there is no cross-protection reaction, and there are multiple subtypes within each serotype. At the center of the virus is a single strand of positive-sense RNA consisting of about 8000 bases, which is the basis of infection and heredity, surrounded by proteins which determine antigenicity, immunity and serological response of the virus; the capsid of the virus is a symmetrical icosahedron. Foot-and-mouth disease virus is the pathogen of foot-and-mouth disease, a highly contagious disease of cloven-hoofed animals. The disease ranks as first in the list 'A' of infectious diseases of animals according to the Office International des Epizooties (OIE) and listed as List A disease in the List of Quarantine Disease for the Animals Imported to the People's Republic of China. As to prevention and treatment of foot-and-mouth disease in China, prevention is mainly through vaccination, and once infected with foot-and-mouth disease, animals will be killed.

"Antigen" refers to a substance that can induce an immune response in the body, that is, it can be specifically recognized and bound by the antigen receptor (TCR/BCR) on the surface of T/B lymphocytes to activate T/B cells and make them proliferate, differentiate and produce immune response products (to sensitize lymphocytes or antibodies), and can specifically bind to the corresponding products in vivo and in vitro.

"Virus-like particles (VLPs)" are particles assembled from one or more viral structural proteins, which have external structures and antigenicity similar to viral particles, but do not contain viral genes.

"VP0, VP3, VP1 antigen proteins of the foot-and-mouth disease virus": FMDV structural protein precursor protein P1 is catalyzed and processed by protease 3C into VP0, VP1 and VP3. These three proteins self-assemble into an icosahedral viral capsid. VP0 protein is the intermediate of P1 after cleavage by protease 3C. VP2 and VP4 are generated by maturation cleavage of VP0, in the last stage of the formation of the viral particle.

The term "vaccine" or "vaccine composition" as used in the present disclosure refers to a pharmaceutical composition containing the FMDV antigen that can induce, stimulate or enhance an immune response of a swine against FMDV.

The term "immunogenic amount" should be understood as an "immunologically effective amount," also refers to an immunoprotective amount or an effective amount to produce an immune response, which is an amount of antigen effective to induce an immune response in a recipient, which immunogenic amount is sufficient to prevent or ameliorate signs or symptoms of a disease including adverse health effects or complications of the disease. The immune response may be sufficient for diagnostic purposes or other tests or may be suitable for use in preventing signs or symptoms of a disease, including adverse health consequences caused by an infection of a pathogen, or complications of the disease. Humoral immunity or cell-mediated immunity or both may be induced. The immune response of the animal to the immunogenic composition may be assessed indirectly, for example, by measuring antibody titers and analyzing lymphocyte proliferation, or directly by monitoring signs or symptoms after challenge with wild-type strains, while protective immunity provided by the vaccine may be assessed by measuring, for example, clinical signs of subjects such as mortality, reduction in morbidity, temperature values, and overall physiological condition, overall health and performance of the subjects. The immune response may include, but are not limited to induction of cellular and/or humoral immunity.

The term "pharmaceutically acceptable carrier" refers to all components other than the FMDVantigen in the vaccine composition of the present disclosure which are carriers or diluents that do not cause irritation to an organism and do not abrogate the biological activity and properties of the administered compounds, preferably an adjuvant. The term "adjuvant" may includes a compound selected from a group consisting of alhydrogel adjuvant, saponins e.g., Quil A. QS-21 (Cambridge Biotech Inc., Cambridge Mass.), GPI-0100 (Galenica Pharmaceuticals, Inc., Birmingham, Ala.), water-in-oil emulsion, oil-in-water emulsion, water-in-oil-in-water emulsion, the polymers of acrylic or methacrylic acid and the copolymers of maleic anhydride and alkenyl derivative. The term "emulsion" may be based in particular on light liquid paraffin oil (European Pharmacopea type); isoprenoid oil such as squalane or squalene oil resulting from the oligomerization of alkenes, in particular of isobutene or decene; esters of acids or of alcohols containing a linear alkyl group, more particularly plant oils, ethyl oleate, propylene glycol di-(caprylate/caprate), glyceryl tri-(caprylate/caprate) or propylene glycol dioleate; esters of branched fatty acids or alcohols, in particular isostearic acid esters. The oil is used in combination with emulsifier to form the emulsion. The emulsifiers are preferably nonionic surfactants, in particular esters of sorbitan, of mannide (e.g. anhydromannitol oleate), of glycol, of polyglycerol, of propylene glycol and of oleic, isostearic, ricinoleic or hydroxystearic acid, which are optionally ethoxylated, and polyoxypropylene-polyoxyethylene block copolymers, in particular the Pluronic products, especially L121. See Hunter et al., The Theory and Practical Application of Adjuvants (Ed. Stewart-Tull, D. E. 5). John Wiley and Sons, NY, pp 51-94 (1995) and Todd et al. Vaccine 15:564-570 (1997). For example, it is possible to use the SPT emulsion described on page 147 of "Vaccine Design, The Subunit and Adjuvant Approach" edited by M. Powell and M. Newman, Plenum Press, 1995, and the emulsion MF59 described on page 183 of the same book. The term "polymers of acrylic or methacrylic acid" preferably are the polymers of acrylic or methacrylic acid which are cross-linked, especially with polyalkenyl ethers of sugars or polyalcohols. These compounds are known by the term carbomer (Trade name, Carbopol) (Phameuropa Vol. 8, No. 2, 1996). Persons skilled in the art can also refer to U.S. Pat. No. 2,909,462 which describes such acrylic polymers cross-linked with a polyhydroxylated compounds having at least 3 hydroxyl groups, preferably not more than 8, the hydrogen atoms of at least three hydroxyls being replaced by unsaturated aliphatic radicals having at least 2 carbon atoms. The preferred radicals are those containing from 2 to 4 carbon atoms, e.g. vinyls, allyls and other ethylenically unsaturated groups. The unsaturated radicals may themselves contain other substituents, such as methyl. The products sold under the name Carbopol; (BF Goodrich, Ohio. USA) are particularly appropriate. They are cross-linked with an allyl sucrose or with allyl pentaerythritol. Among them, there may be mentioned Carbopol 974P, 934P and 971 P, most preferably Carbopol 971P. For the term "copolymerrs of maleic anhydride and alkenyl derivative", EMA (Monsanto), which is the copolymer of maleic anhydride and ethylene, can also be considered. The dissolution of these polymers in water leads to an acid solution that will be neutralized, preferably to physiological pH, in order to give the adjuvant solution, into which the immunogenic, immunological or vaccine composition itself will be incorporated. The term "adjuvant" includes, but is not limited to, the RIB1 adjuvant system (Ribi Inc.), Block co-polymer (CytRx, Atlanta Ga.), SAF-M (Chiron, Emeryville Calif.), monophosphoryl lipid A, Avridine lipid-amine adjuvant, heat-labile enterotoxin from *E. coli* (recombinant or otherwise), cholera toxin, IMS 1314, muramyl dipeptide, and Gel adjuvant among many others. Preferably, the adjuvant includes one or more of white oil, alhydrogel adjuvant, saponins, water-in-oil emulsion, oil-in-water emulsion, water-in-oil-in-water emulsion, the polymers of acrylic or methacrylic acid, the copolymers of maleic anhydride and alkenyl derivative, the RIBI adjuvant system, Block co-polymer, SAF-M, monophosphoryl lipid A, Avridine lipid-amine adjuvant, heat-labile enterotoxin from *E. coli*, cholera toxin, IMS 1314, muramyl dipeptide, Montanide ISA 206 and Gel adjuvant.

"Degenerate sequence": in molecular biology, the phenomenon that a common amino acid has two or more codons is called degeneracy of codon, and such a sequence is called a degenerate sequence.

"Gene recombination": refers to the recombination of genes that control different traits. Modern genetic engineering technology implements genetic recombination in test tubes according to artificial design, also known as recombinant DNA. The purpose is to transfer the genetic gene in one individual cell to the DNA molecule in another individual cell with different traits to cause genetic variation. After target genes from a donor are transferred into a recipient bacterium, a gene product can be expressed to obtain products that are difficult to obtain by ordinary methods.

"Transformation" refers to cause cells or cultured recipient cells to obtain new genetic phenotypes by automatically getting or artificial supplying foreign DNA.

"Transduction" refers to transfer of DNA and recombination of genes occurring between a donor cell and a recipient cell when a virus is released from an infected (donor) cell and re-infects another (recipient) cell.

When referring to FMDV infection the term "prevention and/or treatment" refers to inhibition of replication and spread of FMDV or prevention of FMDV from colonizing its host, and alleviation of disease or symptoms of illness of the FMDV. If the viral load is reduced, the severity of the illness is reduced, and/or the food intake and/or growth are increased, then it can be considered that the treatment has achieved a therapeutic effect.

The description of the present disclosure is further provided as follows with reference to the specific embodiments, and features and advantages of the present disclosure will become more apparent from the following description. However, these embodiments are merely exemplary and do not limit the scope of the present disclosure in any way. It should be understood by a person skilled in the art that modifications or alternatives to details and forms of the technical solution of the present disclosure without deviation from the spirit and scope of the present disclosure will be allowed, while those modifications and alternatives should all fall within the scope of the present disclosure.

The chemical reagents used in the examples of the present disclosure are of analytical grade and are purchased from Sinopharm Group Co. Ltd.

In order to make the present disclosure more understandable, the present disclosure will be further described with reference to specific embodiments. The experimental methods described in the present disclosure are conventional methods unless otherwise specified. The biological materials are commercially available unless otherwise specified.

EXAMPLES

Materials and Methods

Construction and Transformation of Vector

Recombinant vector pET28a-VP0-VP3-VP1 containing VP0, VP3, VP1 genes of type O CATHAY topotype foot and mouth disease virus.

The VP0 gene fragment shown in SEQ ID NO: 1 in the sequence listing, the VP3 gene fragment shown in SEQ ID NO: 2 in the sequence listing, and the VP1 gene fragment shown in SEQ ID NO: 3 in the sequence listing were synthesized by GENEWIZ, Inc. and respectively ligated with pBLUE-T Vector vector, and the successfully ligated recombinant clones were digested with enzymes BamH I/EcoR I, Sac I/Sal I, Hind III/Xho I, and the fragments obtained after digestion were ligated with the pET28a vector digested with the same enzymes.

The ligation product was transformed into DH5a competent cells prepared with CaCl 2 and then the DH5a competent cells were spread onto kanamycin-resistant solid LB medium. When single colonies were clearly visible; a single colony was picked into LB liquid medium containing kanamycin, and cultured at 230 rpm at 37° C. for 12 hours overnight, and the recombinant plasmid pET28a-VP0-VP3-VP1 was extracted.

The above-mentioned recombinant plasmid pET28a-VP0-VP3-VP1 inserted with the VP0, VP3, VP1 genes of type O CATHAY topotype foot-and-mouth disease virus was transformed into 40 μl of competent *E. coli* BL21 (DE3) prepared by the calcium chloride method, which then were spread onto kanamycin-resistant solid LB medium, let stand at 37° C. for 10-12 hours until single colonies were clearly visible; a single colony was picked into a test tube containing 4 ml of kanamycin-resistant liquid LB medium, incubated at 37° C. with shaking at 230 rpm for 12 hours, from which 1 ml of bacterial solution was lyophilized and stored at −80° C.

Recombinant vector containing VP4, VP2, VP3, and VP1 genes of type O SEA topotype foot and mouth disease virus.

The VP4 gene fragment shown in SEQ ID NO: 4 in the sequence listing, the VP2 gene fragment shown in SEQ ID NO: 5 in the sequence listing, the VP3 gene fragment shown in SEQ ID NO: 6 in the sequence listing and the VP1 gene fragment shown in SEQ ID NO: 7 in the sequence listing were synthesized by GENEWIZ, Inc. to construct an *Escherichia coli* expression strain which contains recombinant plasmid pET28a-VP4-VP2-VP3-VP1 and can express tandemly VP4, VP2, VP3, and VP1 genes of type O SEA topotype foot-and-mouth disease virus. The strain was lyophilized and stored at −80° C.

Expression of antigen proteins and identification of type O foot-and-mouth disease virus-like particles.

Type O CATHAY topotype foot-and-mouth disease virus antigen and VLP particles.

The *Escherichia coli* strain with recombinant plasmid pET28a-VP0-VP3-VP1 were taken out from −80° C., inoculated into 50 ml kanamycin-resistant LB liquid medium, cultured at 37° C. with shaking at 230 rpm for 12 hours, then transferred to 1 L LB liquid medium and cultivated at 37° C. to prepare seed broth for fermentation.

The fermentation tank is a 50 L fermentation tank (Shanghai Baoxing Bio-Engineer Equipment Co., Ltd.). 30 L of culture medium was prepared and put into the fermentation tank, sterilized at 121° C. for 30 minutes. On the next day, 5 L of seed broth was introduced to the fermentation tank, and when the concentration of cell culture reached about 10 $OD_{600}$, the culture temperature was lowered to 25° C., and 4 g of IPTG was added to induce expression for 12 hours. The final concentration was about 40 ($OD_{600}$). The fermentation tank was removed and the bacteria were centrifuged to collect.

The bacteria were resuspended, and broken 4 times at a pressure of 800 bar by using a homogenizer, which was then centrifuged at 13500 rpm for 40 min. The supernatant was retained and detected by 15% SOS-PAGE electrophoresis. The protein was roughly purified by ammonium sulfate fractional precipitation, followed by chromatography, and the purified protein was subjected to SOS-PAGE electrophoresis.

The type O CATHAY topotype foot-and-mouth disease virus-like particles were observed through the electron microscope after negative staining with phosphotungstic acid.

SEA-type O-type foot-and-mouth disease virus-like particle antigen and VLP particles.

The *E. coli* strain with recombinant plasmid pET28a-VP4-VP2-VP3-VP1 was taken out from −80° C. and inoculated into 50 ml LB liquid medium resistant to kanamycin, cultured according to the preparation conditions similar to that of the above-mentioned type O CATHAY topotype foot-and-mouth disease virus antigen, and then transferred to 1L LB liquid medium and cultured at 37° C.

A 50L fermentation tank was used for large-scale fermentation and expression of type O SEA topotype foot-and-mouth disease virus antigen under the similar preparation conditions of the above-mentioned type O CATHAY topotype foot-and-mouth disease virus antigen.

The four type O SEA topotype foot-and-mouth disease virus antigens expressed in tandem in the bacteria were separated, purified and identified according to the preparation conditions similar to the above-mentioned type O CATHAY topotype foot-and-mouth disease virus antigen.

The type O SEA topotype foot-and-mouth disease virus-like particles were observed through the electron microscope after negative staining with phosphotungstic acid.

Preparation of O-type foot-and-mouth disease virus-like particle vaccine compositions Vaccine compositions containing type O CATHAY topotype foot-and-mouth disease virus-like particle antigen.

The prepared type O CATHAY topotype foot-and-mouth disease virus-like particle antigen was taken and slowly added to an adjuvant, which was continuously stirred by an emulsifier at 800 rpm for 12 minutes during the process of adding, mixed well and stored at 4° C. Vaccine compositions containing type O CATHAY topotype foot-and-mouth disease virus-like particle antigen were prepared. Adjuvants suitable for use in the present disclosure may be adjuvants known to those skilled in the art. In the present disclosure, the adjuvant ISA 206 (SEPPIC, France) is selected.

Vaccine compositions containing type O CATHAY topotype foot-and-mouth disease virus-like particle antigen and type O SEA topotype foot-and-mouth disease virus-like particle antigen.

The prepared type O CATHAY topotype foot-and-mouth disease virus-like particle antigen and the prepared type O SEA topotype foot-and-mouth disease virus-like particle antigen were taken to prepare vaccine compositions according to the above method of preparing vaccine compositions containing type O CATHAY topotype foot-and-mouth disease virus-like particle antigen. Adjuvants suitable for use in the present disclosure may be adjuvants known to those skilled in the art. In the present disclosure, the adjuvant ISA 206 (France Sepic) is selected.

Immunogenicity analysis of O-type foot-and-mouth disease virus-like particle vaccine compositions.

Immunogenicity of type O CATHAY topotype foot-and-mouth disease virus-like particle vaccine compositions.

The immunogenicity of the antigen in the vaccine compositions was measured with the level of the antibodies in the immunized pigs' serums detected by ELISA.

Healthy and susceptible feeder pigs negative for type O FMDV antibody and antigen with a weight of about 40 kg were selected and immunized with the vaccine compositions containing type O CATHAY topotype foot-and-mouth disease virus-like particle antigen. The immunization route of the immunization groups was intramuscular neck injection of 2 ml of vaccine, and the control group was immunized with the same amount of PBS. Blood samples were collected from each pig before immunization, and on the $7^{th}$, $14^{th}$, $21^{st}$, and $28^{th}$ days after immunization. type O CATHAY topotype foot-and-mouth disease antibody ELISA test kit was used for antibody detection on the collected serum.

Duration test of immunity of type O CATHAY topotype foot-and-mouth disease virus-like particle vaccine compositions.

Duration test of immunity of type O CATHAY type foot-and-mouth disease virus-like particle vaccine compositions.

The durations of immunity of the antigen in the vaccine compositions were measured with the levels of the antibodies in the immunized pigs' serums detected by ELISA.

Healthy and susceptible feeder pigs negative for type O FMDV antibody and antigen with a weight of about 40 kg were selected and immunized with the vaccine compositions containing type O CATHAY topotype foot-and-mouth disease virus-like particle antigen. The immunization route of the immunization groups was intramuscular neck injection of 2 ml of vaccine, and a blank control group was immunized with the same amount of PBS. All pigs were immunized once. Blood samples were collected from each pig before immunization, and on the $21^{st}$, $28^{th}$, $35^{th}$, $77^{th}$, $105^{th}$ and $133^{th}$ days after immunization.

An immunization group for a commercial inactivated vaccine (O/Mya98/XJ/2010 strain+O/GX/09-7 strain) was a control group. The immunization route was intramuscular neck injection of 2 ml of vaccine, and a blank control group was immunized with the same amount of PBS. Before immunization and on the $21^{st}$ day after $1^{st}$ immunization, a blood sample was taken from each of the pigs, followed by $2^{nd}$ immunization. On the $7^{th}$, $14^{th}$, $56^{th}$, $84^{th}$ and $112^{th}$ day after $2^{nd}$ immunization, a blood sample was taken from each of the pigs.

Immunogenicity of vaccine compositions containing type O CATHAY topotype foot-and-mouth disease virus-like particle and type O SEA topotype foot-and-mouth disease virus-like particle.

The immunogenicity of the antigen in the vaccine compositions was measured with the levels of the antibodies in the immunized pigs' serums detected by ELISA.

Healthy and susceptible feeder pigs negative for type O FMDV antibody and antigen with a weight of about 40 kg were selected and immunized with the prepared vaccine compositions containing type O CATHAY topotype foot-and-mouth disease virus-like particle antigen and type O SEA topotype foot-and-mouth disease virus-like particle antigen, of which the immunization route was intramuscular neck injection of 1 ml of vaccine, and the control group was immunized with the vaccine compositions containing type O CATHAY topotype foot-and-mouth disease virus-like particle antigen or the vaccine compositions containing type O SEA topotype foot-and-mouth disease virus-like particle antigen, and the blank control group was immunized with 2 ml of PBS. Blood samples were collected from each pig before immunization, and on the $7^{th}$, $14^{th}$, $21^{st}$, and $28^{th}$ days after immunization.

Example 1 Type O CATHAY Topotype Foot-and-Mouth Disease Virus-Like Particles

The bacterial cells expressing protein antigens were resuspended and detected by SDS-PAGE electrophoresis. Then the expression levels of the three tandemly expressed proteins in the supernatant are all about 20%. As detected by the SDS-PAGE electrophoresis, it showed that the target protein was purified and enriched.

It can be observed through the electron microscope after negative staining with phosphotungstic acid that the type O CATHAY topotype foot-and-mouth disease virus protein has formed virus-like particles, and the formed virus-like particles are plump, with high assembly efficiency and no aggregation. After being placed at 4° C. for 3 months, it can be observed through the electron microscope after negative staining with phosphotungstic acid that the FMD virus-like particles are still plump without aggregation. It shows that the foot-and-mouth disease virus protein prepared by the sequence screened by the present disclosure forms stable virus-like particles.

Example 2 Preparation of Type O CATHAY Topotype Foot-and-Mouth Disease Virus-Like Particle Vaccine Compositions Specific ratio of each component in the prepared vaccines is shown in Table 1.

TABLE 1

Component ratio of type O CATHAY topotype foot-and-mouth disease virus-like particle vaccines

| | Vaccine1 | Vaccine2 | Vaccine3 |
|---|---|---|---|
| Foot-and-mouth disease antigen (μg/ml) | 160 | 200 | 240 |
| ISA 206 adjuvant (V/V %) | 50% | 50% | 50% |

Example 3 Immunogenicity Test of Vaccine Compositions Containing Type O CATHAY Topotype Foot-and-Mouth Disease Virus-Like Particle Antigen 20 healthy and susceptible feeder pigs negative for type O FMDV antibody and antigen with a weight of about 40 kg were selected and randomly divided into 4 groups, 5 pigs per group. Groups 1-3 were immunization groups for corresponding vaccine 1, vaccine 2, and vaccine 3 prepared by Example 2 of the present disclosure, respectively, and group 4 is a blank control group. The immunization route of the immunization groups was intramuscular neck injection of 2 ml of vaccine, and the blank control group was immunized with the same amount of PBS.

The antibody titer results showed that the antibodies of all pigs were negative before immunization with vaccines which could all reach above 1:128 on the 14th day after the first immunization. The antibody of the blank control group was negative and there was no change. The specific results are shown in Table 2.

TABLE 2

Antibody levels of type O CATHAY topotype foot-and-mouth disease virus dectected by ELISA

| Group | Pig No. | Before immunization | Day 7 after immunization | Day 14 after immunization | Day 21 after immunization | Day 28 after immunization |
|---|---|---|---|---|---|---|
| 1 | 1 | <1:8 | 1:64 | 1:128 | 1:360 | 1:360 |
| | 2 | <1:8 | 1:64 | 1:180 | 1:720 | 1:720 |
| | 3 | <1:8 | 1:64 | 1:128 | 1:360 | 1:720 |
| | 4 | <1:8 | 1:64 | 1:128 | 1:360 | 1:720 |
| | 5 | <1:8 | 1:64 | 1:128 | 1:360 | 1:360 |
| 2 | 6 | <1:8 | 1:64 | 1:128 | 1:360 | 1:360 |
| | 7 | <1:8 | 1:64 | 1:128 | 1:360 | 1:720 |
| | 8 | <1:8 | 1:64 | 1:128 | 1:360 | 1:720 |
| | 9 | <1:8 | 1:90 | 1:180 | 1:720 | 1:720 |
| | 10 | <1:8 | 1:64 | 1:180 | 1:720 | 1:720 |

TABLE 2-continued

| Antibody levels of type O CATHAY topotype foot-and-mouth disease virus dectected by ELISA | | | | | | |
|---|---|---|---|---|---|---|
| Group | Pig No. | Before immunization | Day 7 after immunization | Day 14 after immunization | Day 21 after immunization | Day 28 after immunization |
| 3 | 11 | <1:8 | 1:64 | 1:128 | 1:360 | 1:720 |
| | 12 | <1:8 | 1:90 | 1:180 | 1:720 | 1:720 |
| | 13 | <1:8 | 1:64 | 1:180 | 1:720 | 1:720 |
| | 14 | <1:8 | 1:90 | 1:180 | 1:720 | 1:720 |
| | 15 | <1:8 | 1:64 | 1:128 | 1:360 | 1:720 |
| 4 | 16 | <1:8 | <1:8 | <1:8 | <1:8 | <1:8 |
| | 17 | <1:8 | <1:8 | <1:8 | <1:8 | <1:8 |
| | 18 | <1:8 | <1:8 | <1:8 | <1:8 | <1:8 |
| | 19 | <1:8 | <1:8 | <1:8 | <1:8 | <1:8 |
| | 20 | <1:8 | <1:8 | <1:8 | <1:8 | <1:8 |

It shows that the virus-like particles prepared by the present disclosure can quickly form high levels of specific antibodies, and can provide excellent immune protection against type O CATHAY topotype foot-and-mouth disease virus on the $14^{th}$ day after immunization even when the antigen content is 160 μg/ml.

Example 4 Comparative Test of Immunogenicity of Vaccine Compositions Containing Type O CATHAY Topotype Foot-and-Mouth Disease Virus-Like Particle Antigen 20 healthy and susceptible feeder pigs negative for type O FMDV antibody and antigen with a weight of about 40 kg were selected and randomly divided into 4 groups, 5 pigs per group, Group 5 was an immunization group for vaccine 2 prepared by Example 2 of the present disclosure, group 7 was an immunization group for a commercial inactivated vaccine (O/Mya98/XJ/2010 strain+O/GX/09-7 strain), and groups 6 and 8 were blank control groups. The immunization route of group 5 as the immunization group was intramuscular neck injection of 2 ml of vaccine, and group 6 as the blank control group was immunized with the same amount of PBS. Groups 5 and 6 are single-shot immunization. Before immunization and on the $21^{st}$, 28th, 35th, 77th, 105th and 133th days after immunization, blood samples were taken from each of the pigs. The immunization route of group 7 as the immunization group was intramuscular neck injection of 2 ml of vaccine, and group 8 as the blank control group was immunized with the same amount of PBS, Before immunization and on the $21^{st}$ day after $1^{st}$ immunization blood samples were taken for each pig in Groups 7 and 8, and then 2nd immunization was followed. On the 7th, 14th, 56th, 84th and 112th day after 2nd immunization, blood samples were taken from each of the pigs.

The results showed that the antibodies of all pigs were negative before vaccination. On the $21^{st}$ day after the single-shot immunization, the antibodies of the immunization group for vaccine 2 can reach above 1:128, and those of the immunization group for commercial vaccine cannot reach 1:128, which can only reach 1:128 on the $7^{th}$ day after the second immunization; the immunization group for vaccine 2 can still maintain a relatively high antibody level on the 133rd day after the single-shot immunization, while the immunization group for commercial vaccine had an antibody level close to a critical value of immune protection 1:128 on the 112th day after the second immunization. The antibodies of the pigs in the control groups were negative and there was no change. The specific results are shown in Table 3.

TABLE 3

| Comparative result of antibody levels of topotype O CATHAY type foot-and-mouth disease virus detected by ELISA | | | | | | | | |
|---|---|---|---|---|---|---|---|---|
| Group | Pig No. | Before $1^{st}$ immunization | Day 21 after $1^{st}$ immunization | Day 28 after $1^{st}$ immunization | Day 35 after $1^{st}$ immunization | Day 77 after $1^{st}$ immunization | Day 105 after $1^{st}$ immunization | Day 133 after $1^{st}$ immunization |
| 5 | 21 | <1:8 | 1:360 | 1:360 | 1:720 | 1:720 | 1:360 | 1:180 |
| | 22 | <1:8 | 1:720 | 1:720 | 1:720 | 1:720 | 1:360 | 1:360 |
| | 23 | <1:8 | 1:360 | 1:720 | 1:720 | 1:360 | 1:360 | 1:180 |
| | 24 | <1:8 | 1:720 | 1:720 | 1:720 | 1:720 | 1:360 | 1:360 |
| | 25 | <1:8 | 1:720 | 1:720 | 1:720 | 1:720 | 1:360 | 1:360 |
| 6 | 26 | <1:8 | <1:8 | <1:8 | <1:8 | <1:8 | <1:8 | <1:8 |
| | 27 | <1:8 | <1:8 | <1:8 | <1:8 | <1:8 | <1:8 | <1:8 |
| | 28 | <1:8 | <1:8 | <1:8 | <1:8 | <1:8 | <1:8 | <1:8 |
| | 29 | <1:8 | <1:8 | <1:8 | <1:8 | <1:8 | <1:8 | <1:8 |
| | 30 | <1:8 | <1:8 | <1:8 | <1:8 | <1:8 | <1:8 | <1:8 |
| Group | Pig No. | Before $1^{st}$ immunization | Day 21 after $1^{st}$ immunization | Day 7 after $2^{nd}$ immunization | Day 14 after $2^{nd}$ immunization | Day 56 after $2^{nd}$ immunization | Day 84 after $2^{nd}$ immunization | Day 112 after $2^{nd}$ immunization |
| 7 | 31 | <1:8 | 1:45 | 1:360 | 1:720 | 1:360 | 1:180 | 1:180 |
| | 32 | <1:8 | 1:45 | 1:360 | 1:720 | 1:720 | 1:360 | 1:180 |
| | 33 | <1:8 | 1:45 | 1:360 | 1:720 | 1:720 | 1:360 | 1:180 |
| | 34 | <1:8 | 1:45 | 1:180 | 1:360 | 1:360 | 1:180 | 1:180 |
| | 35 | <1:8 | 1:45 | 1:180 | 1:360 | 1:360 | 1:180 | 1:180 |

TABLE 3-continued

Comparative result of antibody levels of topotype O CATHAY type foot-and-mouth disease virus detected by ELISA

| | | | | | | | | |
|---|---|---|---|---|---|---|---|---|
| 8 | 36 | <1:8 | <1:8 | <1:8 | <1:8 | <1:8 | <1:8 | <1:8 |
| | 37 | <1:8 | <1:8 | <1:8 | <1:8 | <1:8 | <1:8 | <1:8 |
| | 38 | <1:8 | <1:8 | <1:8 | <1:8 | <1:8 | <1:8 | <1:8 |
| | 39 | <1:8 | <1:8 | <1:8 | <1:8 | <1:8 | <1:8 | <1:8 |
| | 40 | <1:8 | <1:8 | <1:8 | <1:8 | <1:8 | <1:8 | <1:8 |

The above experiments show that the virus-like particle vaccine composition prepared by the present disclosure, compared with the commercial inactivated whole-virus vaccine, not only can provide fast production of antibodies at a high level to the type O CATHAY topotype foot-and-mouth disease virus-like particle antigen, with an excellent immune protection effect after only a single-shot immunization, but also can significantly increase the duration of immunity and maintain immune protection for a longer time.

Example 5 Type O SEA Topotype Foot-and-Mouth Disease Virus-Like Particles

The bacterial cells expressing protein antigens were resuspended and detected by SDS-PAGE electrophoresis. Then the expression levels of the four tandemly expressed proteins in the supernatant are all about 20%. As detected by the SDS-PAGE electrophoresis, it showed that the target protein was purified and enriched.

It can be observed through the electron microscope after negative staining with phosphotungstic acid that the type O SEA topotype foot-and-mouth disease virus protein has formed virus-like particles, and the formed virus-like particles are plump, with high assembly efficiency and no aggregation. After being placed at 4° C. for 3 months, it can be observed through the electron microscope after negative staining with phosphotungstic acid that the FMD virus-like particles are still plump without aggregation. It shows that the foot-and-mouth disease virus protein prepared by the sequence screened by the present disclosure forms stable virus-like particles.

Example 6 Preparation of Type O Foot-and-Mouth Disease Virus-Like Particle Vaccine Compositions Specific ratio of each component in the prepared vaccines is shown in Table 4. In this embodiment, the adjuvant ISA 206 (SEPPIC, France) is selected.

TABLE 4

Component ratios of type O foot-and-mouth disease virus-like particle vaccine compositions

| | Vaccine4 | Vaccine5 | Vaccine6 | Vaccine7 |
|---|---|---|---|---|
| Type O CATHAY topotype foot-and-mouth disease antigen (μg/ml) | 160 | 200 | 240 | — |

TABLE 4-continued

Component ratios of type O foot-and-mouth disease virus-like particle vaccine compositions

| | Vaccine4 | Vaccine5 | Vaccine6 | Vaccine7 |
|---|---|---|---|---|
| Type O SEA topotype foot-and-mouth disease antigen (μg/ml) | 160 | 200 | 240 | 200 |
| ISA 206 adjuvant (V/V %) | 50% | 50% | 50% | 50% |

Example 7 Immunogenicity Test of Type O Foot-and-Mouth Disease Virus-Like Particle Vaccine Compositions 30 healthy and susceptible feeder pigs negative for type O FMDV antibody and antigen with a weight of about 40 kg were selected and randomly divided into 6 groups, 5 pigs per group. Groups 9-13 were immunization groups for corresponding vaccine 4, 5, 6 and 7 prepared by Example 6 of the present disclosure and vaccine 2 prepared by Example 2, respectively, and group 14 is a blank control group. The immunization route of groups 9, 10 and 11 (groups immunized with vaccines 4, 5 and 6) was intramuscular neck injection of 1 ml of vaccine, the immunization route of group 12 (a group immunized with vaccine 7) and 13 (a group immunized with vaccine 2) was intramuscular neck injection of 2 ml of vaccine, and the control group was immunized with 2 ml of PBS. Before immunization and on the $7^{th}$, $14^{th}$, $21^{st}$, and $28^{th}$ day after immunization, blood samples were taken from each of the pigs.

Use the type O CATHAY topotype Foot-and-Mouth Disease Antibody ELISA Test Kit to detect the relevant antibodies on the sera collected from groups 9, 10, 11, 13 and 14. The results showed that the antibodies of all pigs were negative before vaccination, which levels could all reach above 1:128 on the $14^{th}$ day after a single-shot vaccination. After immunization with the bivalent type O foot-and-mouth disease virus-like particle vaccine composition at an immunogenic amount of 1 ml (half of conventional dosage 2 ml), the antibody level still met or exceeded the antibody levels of the monovalent type O foot-and-mouth disease virus-like particle vaccine composition with an immunogenic amount of 2 ml. The antibodies of the blank control group were negative and there was no change. The specific results are shown in Table 5.

TABLE 5

Antibody levels of type O CATHAY topotype foot-and-mouth disease virus detected by ELISA

| Group | Pig No. | Before immunization | Day 7 after immunization | Day 14 after immunization | Day 21 after immunization | Day 28 after immunization |
|---|---|---|---|---|---|---|
| 9 | 41 | <1:8 | 1:64 | 1:180 | 1:720 | 1:720 |
| | 42 | <1:8 | 1:90 | 1:180 | 1:720 | 1:720 |
| | 43 | <1:8 | 1:64 | 1:128 | 1:360 | 1:720 |
| | 44 | <1:8 | 1:64 | 1:128 | 1:360 | 1:720 |
| | 45 | <1:8 | 1:64 | 1:128 | 1:360 | 1:360 |
| 10 | 46 | <1:8 | 1:64 | 1:128 | 1:360 | 1:720 |
| | 47 | <1:8 | 1:64 | 1:180 | 1:720 | 1:720 |
| | 48 | <1:8 | 1:64 | 1:128 | 1:360 | 1:720 |
| | 49 | <1:8 | 1:90 | 1:180 | 1:720 | 1:720 |
| | 50 | <1:8 | 1:90 | 1:180 | 1:720 | 1:720 |
| 11 | 51 | <1:8 | 1:64 | 1:128 | 1:360 | 1:720 |
| | 52 | <1:8 | 1:90 | 1:180 | 1:720 | 1:720 |
| | 53 | <1:8 | 1:90 | 1:180 | 1:720 | 1:720 |
| | 54 | <1:8 | 1:90 | 1:180 | 1:720 | 1:720 |
| | 55 | <1:8 | 1:64 | 1:128 | 1:360 | 1:720 |
| 13 | 61 | <1:8 | 1:64 | 1:128 | 1:360 | 1:720 |
| | 62 | <1:8 | 1:64 | 1:128 | 1:360 | 1:720 |
| | 63 | <1:8 | 1:64 | 1:128 | 1:360 | 1:360 |
| | 64 | <1:8 | 1:64 | 1:180 | 1:720 | 1:720 |
| | 65 | <1:8 | 1:90 | 1:180 | 1:720 | 1:720 |
| 14 | 66 | <1:8 | <1:8 | <1:8 | <1:8 | <1:8 |
| | 67 | <1:8 | <1:8 | <1:8 | <1:8 | <1:8 |
| | 68 | <1:8 | <1:8 | <1:8 | <1:8 | <1:8 |
| | 69 | <1:8 | <1:8 | <1:8 | <1:8 | <1:8 |
| | 70 | <1:8 | <1:8 | <1:8 | <1:8 | <1:8 |

A type O SEA topotype Foot-and-Mouth Disease Antibody ELISA Test Kit was used to detect the relevant antibodies on the sera collected from groups 9, 10, 11, 12 and 14. The results showed that the antibodies of all pigs were negative before vaccination, which levels could all reach above 1:128 on the 14$^{th}$ day after a single-shot vaccination. After immunization with the bivalent type O foot-and-mouth disease virus-like particle vaccine compositions at an immunogenic amount of 1 ml (half of conventional dosage 2 ml), the antibody levels still met or exceeded the antibody levels of the monovalent type O foot-and-mouth disease virus-like particle vaccine composition with an immunogenic amount of 2 ml. The antibody of the blank control group was negative and there was no change. The specific results are shown in Table 6.

TABLE 6

Antibody levels of type O SEA topotype foot-and-mouth disease virus detected by ELISA

| Group | Pig No. | Before immunization | Day 7 after immunization | Day 14 after immunization | Day 21 after immunization | Day 28 after immunization |
|---|---|---|---|---|---|---|
| 9 | 41 | <1:8 | 1:90 | 1:180 | 1:720 | 1:720 |
| | 42 | <1:8 | 1:90 | 1:180 | 1:720 | 1:720 |
| | 43 | <1:8 | 1:64 | 1:180 | 1:720 | 1:720 |
| | 44 | <1:8 | 1:64 | 1:128 | 1:360 | 1:720 |
| | 45 | <1:8 | 1:64 | 1:128 | 1:360 | 1:360 |
| 10 | 46 | <1:8 | 1:64 | 1:128 | 1:360 | 1:720 |
| | 47 | <1:8 | 1:90 | 1:180 | 1:720 | 1:720 |
| | 48 | <1:8 | 1:64 | 1:180 | 1:720 | 1:720 |
| | 49 | <1:8 | 1:90 | 1:180 | 1:720 | 1:720 |
| | 50 | <1:8 | 1:90 | 1:180 | 1:720 | 1:720 |
| 11 | 51 | <1:8 | 1:64 | 1:128 | 1:360 | 1:720 |
| | 52 | <1:8 | 1:90 | 1:180 | 1:720 | 1:720 |
| | 53 | <1:8 | 1:90 | 1:180 | 1:720 | 1:720 |
| | 54 | <1:8 | 1:90 | 1:180 | 1:720 | 1:720 |
| | 55 | <1:8 | 1:64 | 1:180 | 1:720 | 1:720 |
| 12 | 56 | <1:8 | 1:64 | 1:128 | 1:360 | 1:720 |
| | 57 | <1:8 | 1:64 | 1:180 | 1:720 | 1:720 |
| | 58 | <1:8 | 1:64 | 1:128 | 1:360 | 1:360 |
| | 59 | <1:8 | 1:90 | 1:180 | 1:720 | 1:720 |
| | 60 | <1:8 | 1:90 | 1:180 | 1:720 | 1:720 |
| 14 | 66 | <1:8 | <1:8 | <1:8 | <1:8 | <1:8 |
| | 67 | <1:8 | <1:8 | <1:8 | <1:8 | <1:8 |
| | 68 | <1:8 | <1:8 | <1:8 | <1:8 | <1:8 |
| | 69 | <1:8 | <1:8 | <1:8 | <1:8 | <1:8 |
| | 70 | <1:8 | <1:8 | <1:8 | <1:8 | <1:8 |

The above experiments show that the bivalent O-type foot-and-mouth disease virus-like particles prepared by the present disclosure can quickly form high-level specific antibodies, and can provide good immune protection against type O CATHAY topotype foot-and-mouth disease virus and type O SEA topotype foot-and-mouth disease virus at the same time; it also shows that the bivalent O-type foot-and-mouth disease virus-like particles can produce a faster and better immune response than the monovalent type O foot-and-mouth disease virus-like particles, and a better immune effect can be achieved even with a lower immune dose (half or less than half of a conventional dose).

The foregoing descriptions are merely preferred examples of the present disclosure and are not intended to limit the present disclosure in any form. Although the present disclosure has been disclosed by way of preferred examples, it is to be understood that the disclosure is not limited thereto. A person skilled in the art may make some equivalent variations or modifications to the above-disclosed technical content without departing from the scope of the technical solutions of the present disclosure to obtain equivalent examples. Without departing from the contents of the technical solutions of the present disclosure, any simple modifications, equivalent changes and modifications made to the above examples according to the technical essence of the present disclosure all fall within the scope of the technical solutions of the present disclosure.

The invention claimed is:

1. A type O foot-and-mouth disease virus-like particle vaccine, wherein the type O foot-and-mouth disease virus-like particle vaccine comprises a type O CATHAY topotype foot-and-mouth disease virus-like particle antigen and a pharmaceutically acceptable carrier that includes an adjuvant:

wherein the type O foot-and-mouth disease virus-like particle antigen is a type O CATHAY topotype foot-and-mouth disease virus-like particle antigen, and the type O CATHAY topotype foot-and-mouth disease virus-like particle antigen is assembled by VP0, VP3 and VP1 antigen proteins of a type O CATHAY topotype foot-and-mouth disease virus (FMDV);

wherein the VP0 antigen protein of the type O CATHAY topotype FMDV is encoded by SEQ ID NO: 1 or a degenerate sequence thereof; the VP3 antigen protein of the type O CATHAY topotype FMDV is encoded by SEQ ID NO: 2 or a degenerate sequence thereof; and the VP1 antigen protein of the type O CATHAY topotype FMDV is encoded by SEQ ID NO: 3 or a degenerate sequence thereof;

wherein the type O foot-and-mouth disease virus-like particle vaccine further comprises an immunogenic amount of type O Southeast Asian (SEA) topotype foot-and-mouth disease virus-like particle antigen, and the type O SEA topotype foot-and-mouth disease virus-like particle antigen is assembled by VP4, VP2, VP3 and VP1 antigen proteins of type O SEA topotype FMDV; and wherein the VP4 antigen protein of type O SEA topotype FMDV is encoded by SEQ ID NO: 4 or a degenerate sequence thereof; the VP2 antigen protein of type O SEA topotype FMDV is encoded by SEQ ID NO: 5 or a degenerate sequence thereof; the VP3 antigen protein of type O SEA topotype FMDV is encoded by SEQ ID NO: 6 or a degenerate sequence thereof; and the VP1 antigen protein of type O SEA topotype FMDV is encoded by SEQ ID NO: 7 or a degenerate sequence thereof.

2. The type O foot-and-mouth disease virus-like particle vaccine according to claim 1, wherein the content of the type O CATHAY topotype foot-and-mouth disease virus-like particle antigen is 160-240 μg/ml.

3. The type O foot-and-mouth disease virus-like particle vaccine according to claim 2, wherein the content of the type O CATHAY topotype foot-and-mouth disease virus-like particle antigen is 200 μg/ml.

4. The type O foot-and-mouth disease virus-like particle vaccine according to claim 1, wherein the adjuvant is one or more selected from the group consisting of white oil, aluminum hydroxide adjuvant, saponins, Avridine, didecyl adipate, water-in-oil emulsion, oil-in-water emulsion, water-in-oil-in-water emulsion, polymers of acrylic or methacrylic acid, copolymers of maleic anhydride and alkenyl derivative, Block co-polymer, monophosphoryl lipid A, heat-labile enterotoxin from *E. coli*, cholera toxin, muramyl dipeptide, and a mineral oil adjuvant that is a water-in-oil-in-water (w/o/w) formulation, wherein the content of the adjuvant is 5%-60% V/V.

5. The type O foot-and-mouth disease virus-like particle vaccine according to claim 4, wherein the content of the adjuvant is 30%-60% V/V.

6. The type O foot-and-mouth disease virus-like particle vaccine according to claim 5, wherein the content of the adjuvant is 50% V/V.

7. The type O foot-and-mouth disease virus-like particle vaccine according to claim 1, wherein the content of the type O SEA topotype foot-and-mouth disease virus-like particle antigen is 160-240 μg/ml.

8. The type O foot-and-mouth disease virus-like particle vaccine according to claim 7, wherein the content of the type O SEA topotype foot-and-mouth disease virus-like particle antigen is 200 μg/ml.

9. A method for preparing the type O foot-and-mouth disease virus-like particle vaccine of claim 1, wherein the method comprises:

Step (1) amplifying and cloning respectively genes of VP0, VP3, VP1 antigen proteins of the type O CATHAY topotype foot-and-mouth disease virus into a common tandem expression vector to obtain a recombinant expression vector containing the genes of VP0, VP3, VP1 antigen proteins of the type O CATHAY topotype foot-and-mouth disease virus;

Step (2) transforming or transducing a host cell with the recombinant expression vector containing genes of VP0, VP3, VP1 antigen proteins of the type O CATHAY topotype foot-and-mouth disease virus obtained in step (1) to obtain a recombinant containing the recombinant expression vector;

Step (3) culturing the recombinant obtained in step (2), expressing the VP0, VP3, VP1 antigen proteins of the type O CATHAY topotype foot-and-mouth disease virus in tandem which then self-assemble to form the type O CATHAY topotype foot-and-mouth disease virus-like particle antigen; and Step (4) purifying the type O CATHAY topotype foot-and-mouth disease virus-like particle antigen obtained in step (3) and adding an adjuvant.

10. The method according to claim 9, wherein the VP0 antigen protein of type O CATHAY topotype FMDV is encoded by SEQ ID No: 1 or a degenerate sequence thereof; the VP3 antigen protein of type O CATHAY topotype FMDV is encoded by SEQ ID No: 2 or a degenerate sequence thereof; and the VP1 antigen protein of type O CATHAY topotype FMDV is encoded by SEQ ID No: 3 or a degenerate sequence thereof; and wherein the host cell in step (2) is *E. coli* and the VP0, VP3, VP1 antigen proteins of the type O CATHAY topotype FMDV expressed in step (3) are intracellular soluble proteins.

11. The type O foot-and-mouth disease virus-like particle vaccine according to claim 1, wherein the vaccine is part of a medicament for preventing and/or treating type O foot-and-mouth disease.

* * * * *